United States Patent [19]
Shaw

[11] Patent Number: 5,447,434
[45] Date of Patent: Sep. 5, 1995

[54] MICROMECHANICAL SEAL

[76] Inventor: Leon Shaw, 1225 Broken Sound Pkwy. NW., Boca Raton, Fla. 33487

[21] Appl. No.: 194,851

[22] Filed: Feb. 14, 1994

[51] Int. Cl.⁶ .............................................. A61C 8/00
[52] U.S. Cl. .................... 433/173; 403/285; 411/924.1
[58] Field of Search ............... 433/173, 174, 175, 176; 411/8, 333, 334, 335, 360, 542, 924.1; 403/282, 285; 285/382.1, 382.2

[56] References Cited

U.S. PATENT DOCUMENTS

| | | | |
|---|---|---|---|
| 4,850,870 | 7/1989 | Lazzara et al. | 433/173 |
| 4,850,873 | 7/1989 | Lazzara et al. | 433/173 |
| 5,098,294 | 3/1992 | Lee et al. | 433/173 |
| 5,328,371 | 7/1994 | Hund et al. | 433/173 |

FOREIGN PATENT DOCUMENTS 1229507  4/1971  United Kingdom ..................... 411/8

*Primary Examiner*—Cary E. O'Connor
*Attorney, Agent, or Firm*—M. K. Silverman

[57] ABSTRACT

A micromechanical seal between a first body and a second body, which is axially threadably securable to the first body, is formed by the combination of a first annular concave radial surface upon the first body, the first surface defining a radius of curvature in the range of about two to about eight ten-thousandths of an inch, a second annular concave radial surface upon the second body, the second surface fully complemental in inner and outer radial dimensions to the first surface, the second surface defining a radius of curvature in the range of about two to about eight ten-thousandths of an inch. Upon tightening of the respective axially threadedable surfaces of the first and second bodies, a micromechanical seal in a region of compression, formed by the opposing concave surfaces, is created.

11 Claims, 1 Drawing Sheet

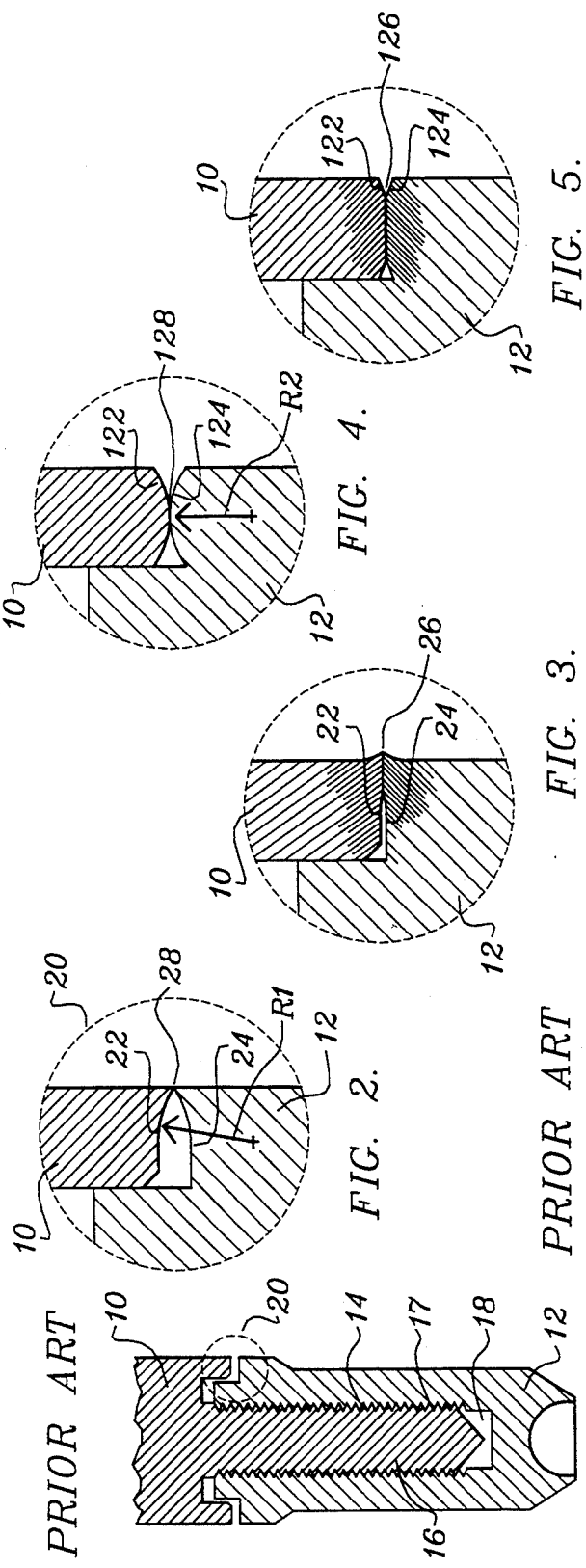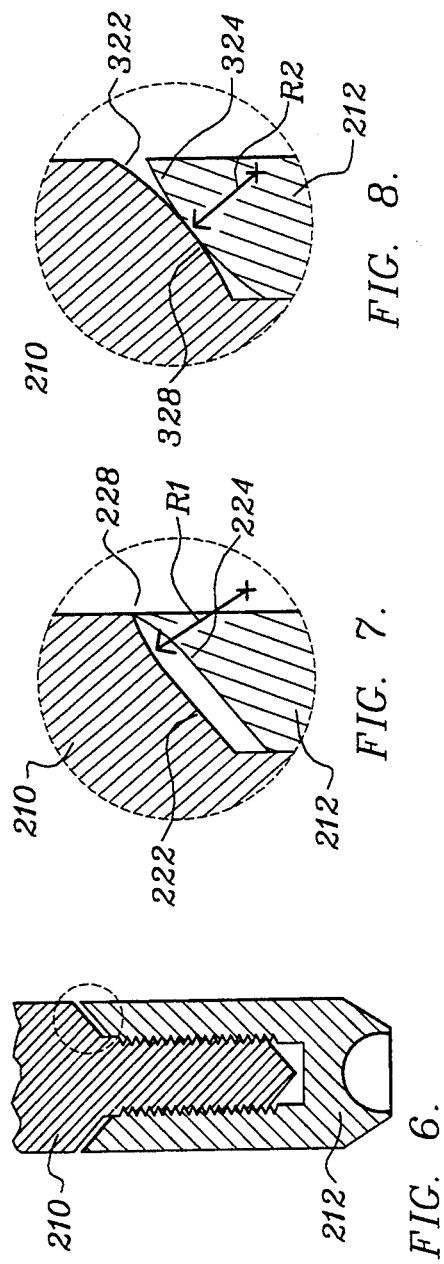

MICROMECHANICAL SEAL

BACKGROUND OF THE INVENTION

The present invention relates to micromechanical seals and, more particularly, to seals of the type having particular utility in the area of dental implants where it is particularly important to effect a durable closure between the abutment and implant portions of a dental implant system.

The importance of, and requirement for, such a seal at the interface between the abutment and implant portions arise because of the need to prevent penetration of such interface by bacteria and microscopic debris to which such dental structures are continually subject.

To the knowledge of the inventor there does not exist any method or means of effecting a micromechanical seal other than the use of a chemical bond which, itself, is subject to degradation in the course of normal use in a dental system.

The present invention thereby addresses the long felt need in art of dental implants to provide a micromechanical seal at the interface between the abutment and implant portions of a dental system without requirement for the use of chemical adhesives or washer equivalents for the accomplishment of such a seal.

SUMMARY OF THE INVENTION

The instant invention constitutes a micromechanical seal between a first body and a second body which is axially threadably securable to said first body. A seal between said first and second bodies is formed by the combination of (a) a first annular concave radial surface upon said first body, said first surface defining a radius of curvature in the range of about two (2) to about eight (8) ten-thousandths of an inch, and (b) a second annular concave radial surface upon said second body, said second surface fully complemental in inner and outer radial dimensions to said first surface, said second surface defining a radius of curvature in the range of about two (2) to about eight (8) ten-thousandths of an inch. Upon tightening of the respective axially threadable surfaces of said first and second bodies, a micromechanical seal in a region of compression, formed by said opposing concave surfaces, is created.

It is, accordingly, an object of the present invention to provide an improved micromechanical seal between bodies having a selectably threadably securable surfaces therebetween.

It is another object to provide an improved micromechanical seal between components of a dental implant system.

It is a further object to provide an improved means of sealing between abutment and implant portions of a dental system.

The above and yet other objects and advantages of the invention will become apparent from the hereinafter set forth Brief Description of the Drawings, Detailed Description of the Invention and claims appended herewith.

BRIEF DESCRIPTION OF THE DRAWINGS

FIG. 1 is an axial. cross-sectional view of a prior art dental abutment and implant.

FIG. 2 is an enlarged view of the region of the abutment-implant interface, shown in dotted circle in FIG. 1 and also showing the inventive improvement.

FIG. 3 is an assembly view of FIG. 2 showing in the compressed area of interface of the portions of the implant system.

FIG. 4 is a view, similar to the view of FIG. 2, however, showing a second embodiment of the instant invention.

FIG. 5 is an assembly view of FIG. 4 showing the area of compression thereof.

FIG. 6 is an axial cross-sectional view of a different form of prior art dental abutment and implant.

FIG. 7 is an enlarged view of the area of the implant system of FIG. 6 to which the invention is applicable, said view corresponding to the embodiment of FIGS. 2 and 3, FIG. 8 is an enlarged view of the embodiment of FIGS. 4 and 5 as applied to the implant system of the type of FIG. 6.

DETAILED DESCRIPTION OF THE INVENTION

With reference to the axial cross-sectional view of FIG. 1 there is shown a typical prior art dental implant system consisting of an abutment portion 10 and an implant portion 12. Therein, as may be noted, there is provided a first threaded axial surface 14 upon member 16 of abutment portion 10 and, conversely, a complemental axially threadable surface 17 upon bore 18 of said implant portion 12. Thereby, in the manner shown in FIG. 1, abutment portion 10 is axially threadably securable into bore 18 of implant portion 12 along said respectively complementally threadable surfaces 14 and 17.

In the view of FIG. 1 the respective abutment and implant portions are shown in a partially axially secured condition so that the area of interface 20 between said abutment and implant portions may be viewed in greater detail, with reference to the inventive micromechanical seal, in FIG. 2. As may, more particularly, be noted therein, interface surface 22 of abutment 10 is provided with a radius R1 which is in the range of between about two (2) and about eight (8) ten-thousandths of an inch, with a radius of five (5) ten-thousandths of an inch (13 micrometers) comprising the preferred embodiment of the invention.

Conversely, interface surface 24 of implant portion 12 is provided with a similar concave radius which is in the same range of two (2) to eight (8) ten-thousandths of an inch as is said opposing interface surface 22 of the abutment portion 10 said surface 24 also having a preferred embodiment of five ten-thousandths of an inch. It is noted that the entire radial geometry of surfaces 22 and 24 are fully complemental to each other.

The result of fully advancing abutment portion 10 into implant portion 12, when the opposing concave surfaces 22 and 24 are employed, is shown in the view of FIG. 3. Therein, as may be noted, a micromechanical seal 26, caused by material compression at point 28 in FIG. 2, is created. Said seal 26 is, as may be appreciated, an area of enhanced material density.

In the view of FIG. 4 is shown a further embodiment of the present invention in which a radius R2 is provided to the opposing surfaces 122 and 124 to create micromechanical seal 126 (see FIG. 5) at point 128 which is a tangent of said surfaces 122 and 124. In this embodiment, the micromechanical seal 126 is formed slightly radially inwardly of said seal 26 in the embodiment of FIGS. 2 and 3.

With reference to FIG. 6 there is shown another type of prior art dental system which includes abutment portion 210 and implant 212. Therein, opposing concave surfaces 222 and 224 are each provided with said radius R1 discussed above, The principles of operation thereof follow that above-described with reference to the embodiments of FIGS. 2 and 3. Accordingly, at point 228 of FIG. 7, a micromechanical seal is formed after the abutment portion 210 is fully axially secured into implant portion 212.

In the view of FIG. 8 is shown an embodiment with reference to the prior art structure of FIG. 6 which is similar to the above-described embodiment of FIGS. 4 and 5. Therein opposing concave surface 322 and 324 form a micromechanical seal at point 328 after the portions 210 and 212 have been fully axially secured to each other.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the claims appended herewith,

Having thus described my invention what I claim as new, useful and non-obvious and, accordingly, secure by Letters Patent of the United States is:

1. A micromechanical seal between a first body and a second body which is axially threadably securable about a part of said first body, said seal comprising:
   (a) a first annular concave radial surface, upon said first body, said surface defining a radius curvature in the range of between about two (2) to about eight (8) ten-thousandths of an inch; and (b) a second annular concave radial surface, upon said second body, having fully complemental inner and outer radial dimensions to said first radial surface of said first body, said second annular concave surface defining a radius of curvature in the range of about two (2) to about (8) eight ten-thousandths of an inch,
whereby, upon complete axial threadable securement of said first body into said second body, a region of compression of the material of said first and second bodies will be created at the outermost radial points of said first and second annular concave surfaces.

2. The micromechanical seal as recited in claim 1, in which said first body is a dental abutment and said second body is a dental implant, each of a dental implant system.

3. The seal system as recited in claim 2, in which said radius of curvature of said first and second radial surfaces are about five ten-thousandths of an inch.

4. The seal system as recited in claim 2, in which said first and second surfaces comprise respective male and female shoulders of said abutment and implant portions of an implant system.

5. The seal system as recited in claim 4, in which each of said bodies comprise medical grade titanium.

6. The seal system as recited in claim 1, is which said respective concave surfaces define, prior to full axial securement of said first body into said second body, a mutual tangent point at an outermost radial dimension of each of said annular concave surfaces.

7. A micromechanical seal between a first body and a second body which is axially threadably securable about a part of said first body, said seal comprising:
   (a) a first annular convex radial surface, upon said first body, said surface defining a radius curvature in the range of between about two (2) to about eight (8) ten-thousandths of an inch; and
   (b) a second annular convex radial surface, upon said second body, having fully complemental inner and outer radial dimensions to said first radial surface of said first body, said second annular convex surface defining a radius of curvature in the range of about two (2) to about (8) eight ten-thousandths of an inch,
whereby, upon complete axial threadable securement of said first body into said second body, a region of compression of the material of said first and second bodies will be created at a tangent point of said first and second annular convex surfaces.

8. The micromechanical seal as recited in claim 7, in which said first body is a dental abutment and said second body is a dental implant, each of a dental implant system.

9. The seal system as recited in claim 8, in which said radius of curvature of said first and second radial surfaces are about five ten-thousandths of an inch.

10. The seal system as recited in claim 8, in which said first and second surfaces comprise respective male and female shoulders of said abutment and implant portions of an implant system.

11. The seal system as recited in claim 10, in which each of said bodies comprise medical grade titanium.

* * * * *